United States Patent [19]

Richard, Jr. et al.

[11] Patent Number: 5,649,326

[45] Date of Patent: Jul. 22, 1997

[54] FLEXIBLE HYDROPHILIC COATING FOR ORTHOPAEDIC CASTING GLOVES AND METHOD FOR MAKING SUCH GLOVES

[75] Inventors: Robert Edward Richard, Jr., Plainville; Hee Kyung Yoon, North Easton, both of Mass.

[73] Assignee: Johnson & Johnson Professional, Inc., Raynham, Mass.

[21] Appl. No.: 341,821

[22] Filed: Nov. 18, 1994

[51] Int. Cl.$^6$ ............................................. A41D 19/00
[52] U.S. Cl. .............................. 2/161.7; 2/167; 2/168; 524/503
[58] Field of Search ..................... 2/161.7, 167, 168, 2/159; 428/522; 524/55, 503

[56] References Cited

U.S. PATENT DOCUMENTS

| | | | |
|---|---|---|---|
| 3,241,501 | 3/1966 | Watts | 105/369 |
| 3,881,473 | 5/1975 | Corvi et al. | 128/90 |
| 4,047,251 | 9/1977 | Stockum | 2/168 |
| 4,100,309 | 7/1978 | Micklus et al. | 427/2 |
| 4,119,094 | 10/1978 | Micklus et al. | 128/132 R |
| 4,135,867 | 1/1979 | Stockum | 425/275 |
| 4,550,126 | 10/1985 | Lorenz | 521/159 |
| 4,608,187 | 8/1986 | Chang | 252/90 |
| 4,667,661 | 5/1987 | Scholz et al. | 128/90 |
| 4,774,937 | 10/1988 | Scholz et al. | 128/90 |
| 4,977,901 | 12/1990 | Ofstead | 128/772 |
| 5,088,125 | 2/1992 | Ansell et al. | 2/167 |
| 5,128,168 | 7/1992 | Shlenker et al. | 2/161.7 X |
| 5,196,263 | 3/1993 | Melby et al. | 2/168 X |
| 5,438,709 | 8/1995 | Green et al. | 2/167 |
| 5,439,439 | 8/1995 | Green et al. | 602/6 |

FOREIGN PATENT DOCUMENTS

| 1578895 | 11/1977 | United Kingdom . |
|---|---|---|
| WO81/00671 | 3/1981 | WIPO . |

OTHER PUBLICATIONS

DE 2357931A Abstract May 1975.
DE 2353212A Abstract Apr. 1975.

*Primary Examiner*—Daniel Zirker
*Attorney, Agent, or Firm*—Joseph F. Shirtz

[57] ABSTRACT

A lubricous glove is disclosed wherein the lubricous glove is made of a base material having a coating thereon of a hydrophilic lubricant mixed with a substantial portion of the material of the base material. For example, a natural rubber latex glove may have coated thereon a mixture of natural rubber latex and polyvinyl alcohol in order to provide a lubricous surface. In an alternate embodiment disclosed, the glove may be itself made of a mixture of the flexible base material and the hydrophilic lubricant. For example, a natural rubber latex may be mixed with either polyvinyl alcohol, polyvinylpyrrolidone or polyethylene oxide and a glove formed from the mixture in order to provide a lubricous glove.

22 Claims, 2 Drawing Sheets

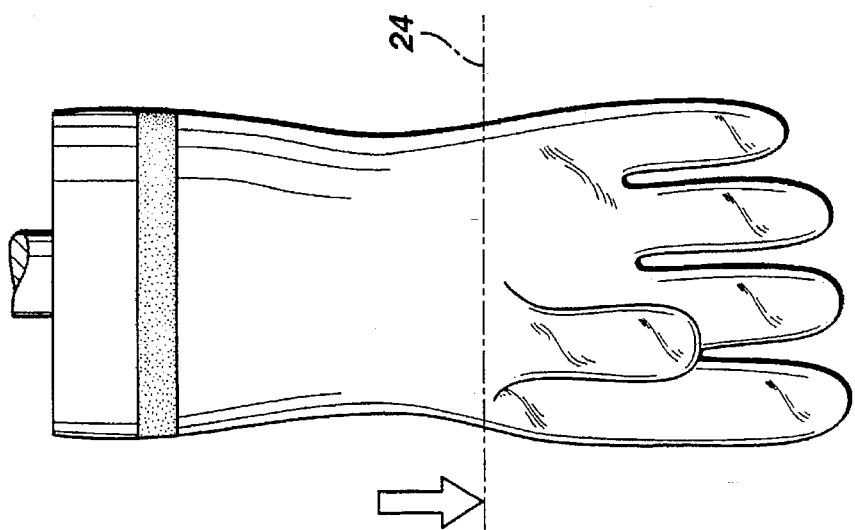
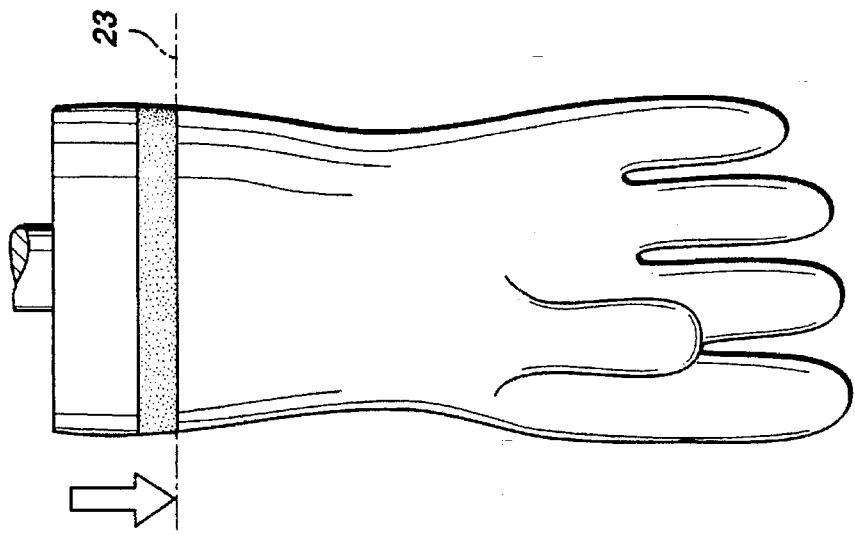
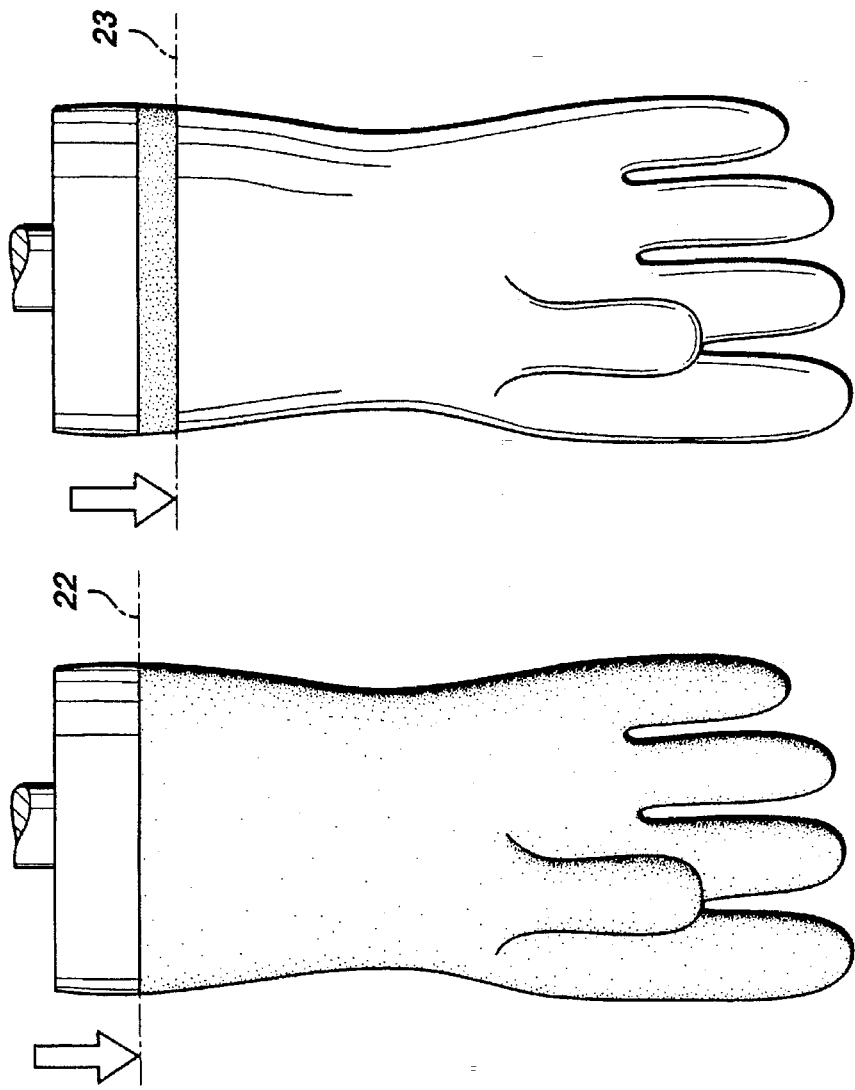

FLEXIBLE HYDROPHILIC COATING FOR ORTHOPAEDIC CASTING GLOVES AND METHOD FOR MAKING SUCH GLOVES

FIELD OF THE INVENTION

The present invention relates to lubricous gloves for applying orthopaedic casting bandages of the type used to form orthopaedic casts. In particular, the invention relates to a coated glove having a lubricous coating which is flexible to resist cracking while assisting in the application of orthopaedic bandages of the type having an uncured resin coating thereon.

BACKGROUND OF THE INVENTION

The present invention relates to copending, commonly assigned U.S. patent application Ser. No. 07/854,146, filed Mar. 20, 1992, now U.S. Pat. No. 5,438,709 entitled "Lubricous Gloves and Method of Making Lubricous Gloves".

Plaster of Paris casts have been used to immobilize body members for some time. These bandages are made by depositing plaster of Paris on a reinforcing scrim material such as gauze. When the plaster of Paris is dipped in water, reactions take place which result in the hardening of the cast material. Plaster of Paris casts, however, suffer from a number of disadvantages. X-ray transmission through the cast to determine whether a fracture has properly set is extremely difficult. In addition, the cast is quite heavy and restricts the mobility of patients wearing the cast.

In order to overcome the disadvantages of plaster of Paris casts, numerous attempts have been made to develop plastic or plastic-reinforced material as replacements for plaster of Paris. U.S. Pat. Nos. 3,241,501 and 3,881,473 disclose casts which are made with a flexible fabric impregnated with a polymer which is capable of being cured by ultraviolet light.

Other attempts to replace plaster of Paris casts are disclosed in German Offenlegenscrift Nos. 2353212 and 2357931, U.K. Patent No. 1,578,895 and PCT Application No. WO81/00671. These casting tapes are open-weave fabrics coated with polyurethane prepolymers, that is, reaction products of isocyanates and polyols. The tapes are dipped into water in the same manner as the plaster of Paris and then applied to the limb of the patient. The water causes the prepolymer to polymerize and form a rigid polymer structure.

More recently, it has been found that in working with such materials having prepolymer resin coating that the tackiness of the resin of the tapes can make working with the tapes difficult and cumbersome for the doctor. In an attempt to address this issue, a glove lubricant comprised of water, sorbitol, mineral oil and silicone fluid has been sold by 3-M Company, St. Paul, Minn., under the tradename Cast Cream™ with instructions to apply the lubricant to the gloves of one applying an isocyanate-functional prepolymer coated cast after wrapping of the cast but before molding of the cast to avoid having the exposed casting material adhere to the gloves of the one applying the cast. This is disclosed in the background of U.S. Patent Nos. 4,667,661 and 4,774,937.

The '661 and '937 patents are directed to addressing the adherence issue by providing the resin itself with a lubricant. The curable resin-coated sheet is prelubricated with a lubricant which is either a) bonded to the resin; b) added to resin or applied to the surface of the coated sheet; or c) provided in a combination of the bonding and surface application described. In many instances, however, the tacky feature of the orthopaedic casting tape is desirable. As by way of example, when the applier is attempting to get the end of the tape or bandage to stick to the surface of the casting tape wrap in order to terminate the application of the tape. The addition of lubricant in the resin permits relative slipping of the resin-coated sheet but requires molding the cast in position and holding it in position to prevent slippage.

Coatings for substrates having a lower coefficient of friction have been shown in U.S. Pat. No. 4,100,309 entitled, "Coated Substrate Having a Low Coefficient of Friction Hydrophilic Coating and a Method of Making the Same". That reference describes a substrate which is coated with a polyvinylpyrrolidone-polyurethane interpolymer. Copending commonly assigned U.S. patent application Ser. No. 726,449, now U.S. Pat. No. 5,439,439 filed Jul. 8, 1991, entitled, "Method of Applying an Orthopaedic Bandage" discloses the use of a polyvinylpyrrolidone coated glove in the application of resinous substrate casting materials. Although the invention described in that application represents a significant advance in the science of orthopaedic casting tapes, there have been certain shortcomings discovered regarding those gloves. That is, the slipperiness of the gloves is present to such a great extent that ancillary manipulation is restricted. The ability of the applier of the casting material to handle pens and other utensils or to tear open foil packages to access the casting material is greatly restricted by the extreme slipperiness of the gloves. Certain other lubricous gloves, for example, polyvinylpyrrolidone-polyurethane coated gloves may have such a slippery surface that handling of the tape roll itself was clumsy. Furthermore, the durability of the gloves is at a point that is less than optimum.

For example, gloves may lose the slippery characteristics completely after applying a few rolls of fiberglass casting tape. Often on large casts multiple tapes must be applied to create a finished cast structure. Thus, the practitioner would have to change gloves in the middle of wrapping a cast which is inconvenient. This loss of functionality is partly due to poor adhesion of the top coat to the base elastic glove, such as natural rubber glove. Also, the elastic modulus of the top coat and the substrate may be widely different. In particular, during the glove making process, stripping of the coated natural rubber glove requires the glove to be stretched greatly. In this case, delamination of the top coat may occur at places where the stretch was the greatest. The same kind of delamination may take place while donning the glove. The delaminated spots are often the areas that show the loss of slip and result in portions of the glove sticking to the casting material during the wrapping process. The delamination is more frequent with a stiffer top coat than with a more flexible top coat. In many cases, portions of the delaminated area are separated entirely from the glove surface exposing an unlubricated glove surface to the casting material.

Poly(vinyl alcohol) (PVA) coated gloves have been found to have outstanding durability and slip characteristics. However, the preferred, or most effectual thermally reversible gelling agent used in existing poly(vinyl alcohol) glove manufacture is toxic and not applicable to medical gloves.

Commonly assigned U.S. patent applications Ser. No. 07/854,146, mentioned above describes a poly(vinyl alcohol) coated glove used for applying casting material which has a thickener added to the coating in order to improve the processability and use of the coating.

It is known that a number of hydrophilic polymers exist which have been used to provide a lubricated surface for applications such as catheters and guidewires used in medical applications. These applications traditionally use polymers such as PVP and PEO which are known to provide a lubricous surface when in an aqueous environment. A problem typically encountered with these polymers is the loss of slippery properties due to a combination of the solubility of these polymers in water at ambient temperatures and the wear which they experience in use. In order to improve the performance or longevity of these coatings, crosslinking has been used to provide a chemical bond which would lead to a coating with reduced water solubility. This has been accomplished using polyisocyanate reagents (U.S. Pat. Nos. 4,100,309; 4,119,094 and 4,550,126), high energy radiation [A. Henglein, Journal of Physical Chemistry, 63, 1052 (1959)] as well as a free radical initiators [British Patent No. 1,022,945, and C. C. Anderson et al., Journal of Applied Polymer Science 23, 2453-2462 (1979)].

Hydrophilic coatings which do not require chemical modification have been disclosed (U.S. Pat. No. 4,977,901). These are based on the ability of the polymer to crystallize on heat treatment such that the crystallites serve as physical crosslinks and prohibit the dissolution of the coating when in contact with water at ambient temperatures, even when the coating is subjected to frictional forces. The crystallization of polymer coatings results from the inherent chemical structure of the polymers and thus is limited to a small group of polymers. A common semi-crystalline polymer which also exhibits slippery properties when in an aqueous environment is PVA. PVA possesses uncommon solubility properties in that it only dissolves in water at elevated temperatures due to the strong hydrogen bonding between polymer chains in the dried state.

Although PVA can be used to provide a lubricous surface and serve effectively in applications such as casting gloves and other articles requiring a hydrophilic surface, the semi-crystalline nature of this polymer as well as its hydrogen bonding capability result in physical properties characterized as stiff, brittle, and inflexible. As a result, coating flexible articles with PVA results in a stiffening of the flexible substrate and may lead to an alteration of the performance of such article. In the case of a latex casting glove, the stretchability of the glove is severely reduced resulting in the alteration of the intended size of the glove as determined on the form from which it is made. For example, a large sized latex glove is reduced in size to that of a medium when coated with a PVA coating. Additionally, the processing of the gloves coated with PVA is complicated due to PVA's stiffness which can lead to abnormally slow production rates and a high defect rate when the gloves are manually removed from the glove forms. Furthermore, the stiff coating prohibits the use of automated glove processing technologies which remove the glove from the hand form by air jets which partially inflate the gloves.

PVA may be made flexible by using a number of chemical plasticizers, such as water, glycerin, ethylene glycol, Urea, ethanolamines, and other glycols and diols. In addition, humectants have also been used to flexibilize PVA by virtue of their water absorbing properties and the fact that water is the most effective plasticizer for PVA. Glycerin has been widely used as a plasticizer for PVA due to its low toxicity and its low vapor pressure compared to water, ethylene glycol, or others. The addition of glycerin leads to a softening and thus enhances the flexibility of PVA, especially in the case of PVA films. It has been found, however, that some glycerin can evaporate during a high temperature processing. Even in the presence of glycerin, it has been observed that low humidity conditions lead to a glove coating with poor flexibility and undesirable physical properties. In addition, it has been determined that although high levels of glycerin lead to more flexible PVA films, it also leads to a softening of these films, and to an enhancement of their solubility in water at ambient temperatures. This is especially true where the films are exposed to frictional forces where abrasion can quickly destroy the film. U.S. Pat. No. 4,608,187 describes the rubber toughening of PVA film compositions through the blending of rubbery materials with a glass transition less than 9° to −18° C. to form flexible PVA pouches or envelopes used to deliver detergents in laundering applications. This disclosure describes that the PVA rubber blends result in the formation of discrete, rubbery microdomains which provide the PVA with a significant increase in flexibility. It is further disclosed that the mechanism of rubber toughening is believed to be related to the partial incompatibility of the PVA and rubber resulting in microscopic crazing of the PVA/rubber blend matrix leading to improved low temperature flexibility.

SUMMARY OF THE INVENTION

The object of the invention is to provide a casting glove which can be prepared by overdipping a latex glove with a PVA coating which has improved flexibility in the dry state. The coating thus allows a latex casting glove to undergo considerable extension without disturbing the integrity of the coating. Due to the chemical structure and physical properties of PVA in the dry state, it is otherwise difficult to manufacture, process, and utilize a latex article such as a glove without undertaking difficult measures. The improved flexibility of the coating thus leads to a number of advantages over the prior art in casting technology related to both performance and economics.

PVA is well-known for its excellent film-forming properties, as well as for its ability to create a hydrophilic surface for the purpose of providing a lubricating surface. In order to maintain the integrity of this surface and prevent its dissolution while in an aqueous environment, attempts have been made to crosslink or insolubilize the PVA through reaction with its pendant hydroxyl groups. This has been accomplished using a number of reagents that will react with hydroxyls such as polyisocyanates, dialdehydes, diacids, diesters, titanates, zirconates, as well as urea or melamine formaldehyde resins. While these reagents perform well as insolubilizers, they also alter the physical properties of the PVA by making it less flexible. The solubility of PVA in aqueous solution can also be lowered by subjecting the PVA to a heat treatment process which results in the annealing of the PVA and the formation of small crystallites which serve as physical crosslinks which prevent the PVA from dissolving in water at ambient temperature. However, crystallization also results in a decrease in the flexibility of the PVA. The introduction of plasticizers can be used to improve the flexibility, however excess amounts of plasticizer can lead to a weakening of the PVA with a resulting decrease in the durability of the film, especially when a frictional force is applied.

The present invention discloses a method to significantly improve the flexibility of a PVA film which is coated onto a latex article such as a glove used for the application of polyurethane casting tapes. The invention further results in improvements in the flexibility without compromising the performance of the PVA coating in terms of its ability to apply the required number of casting tapes without experiencing the adhesion of the glove to the tacky prepolymer prior to its curing. The flexibility of the PVA coating when applied to a latex article such as a glove also allows for the economical manufacture of the article by reducing limitations on production rates as is experienced when a glove must be carefully removed to avoid damage to the coating in a manual operation. It further creates the opportunity for the use of automated equipment for the processing of the glove using methods such as air striping where air jets are used to partially inflate the glove and thus remove it from a hand form. In addition, the alteration of the glove sizing as governed by the glove form size (small, medium, large, and extra large) is not evident as compared to the previous art.

BRIEF DESCRIPTION OF THE DRAWINGS

The invention will be described with reference to the accompanying drawings wherein:

FIG. 2A–C is a schematic drawing showing the dip process on the surface of the glove to form the various constituent parts of the process.

DETAILED DESCRIPTION OF THE INVENTION

Figure 1:
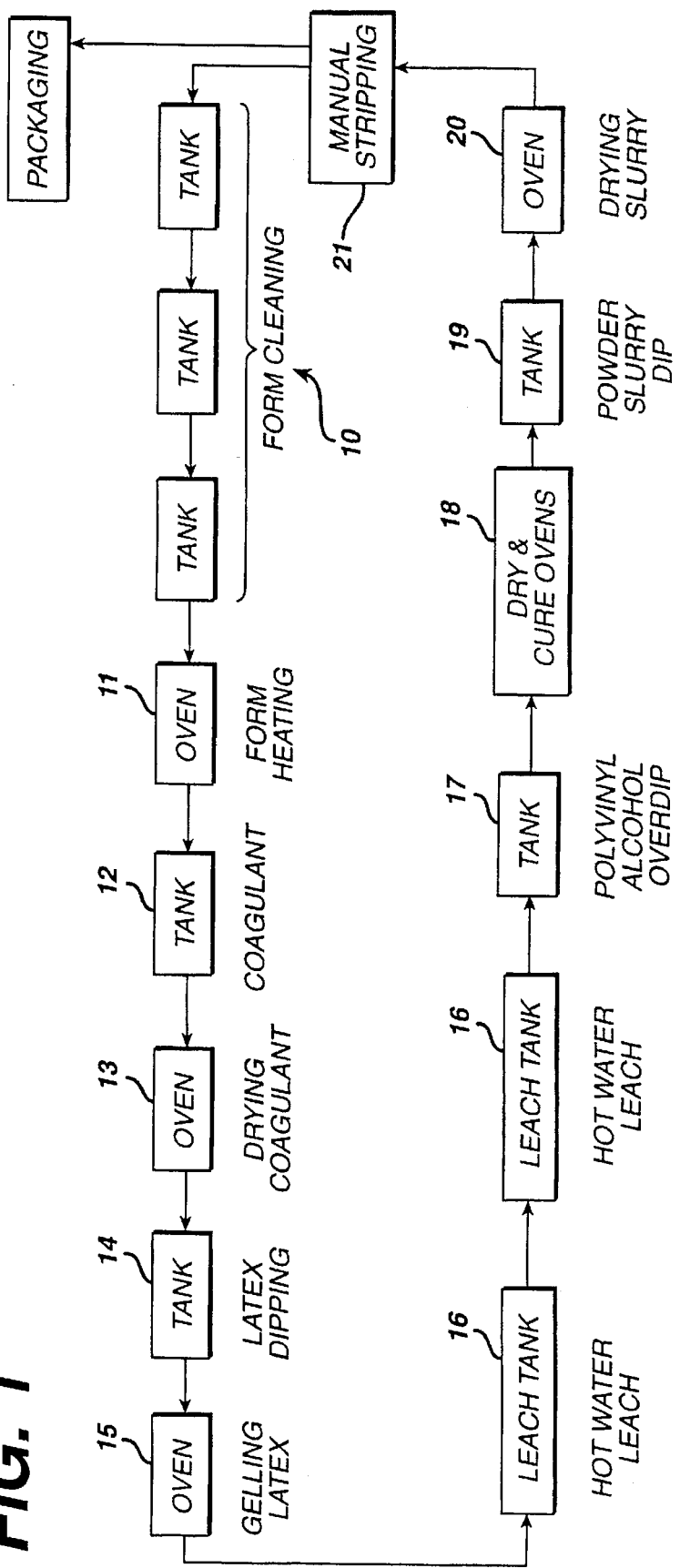
FIG. 1 is block diagram of the process for making the gloves of the present invention.

With reference to FIG. 1, there is shown a block diagram of a general glove-making process initially using the forms which may be forms as described in U.S. Pat. Nos. 4,047,251 and 4,135,867 to Stockum. The form is cleaned prior to initiation of the manufacturing process in order to assure a good forming surface, and the form is passed through an oven 11 to preheat the form. The form itself is dipped into a coagulant tank containing a latex coagulant usually a solution of calcium nitrate and alcohol and calcium nitrate and water. The form is removed from the coagulant tank and proceeds through a drying oven 13. The form, at this time, may be manipulated and rotated 180° into an upright position in order to cause an evening of the coagulant layer prior to drying. The form, with the dry coagulant thereon, is then immersed in a latex solution 14. The presence of the coagulant causes the latex compound to deposit on the form and the form is removed from the latex solution tank. After removal from the latex solution tank, the form is often manipulated again into an upright position or otherwise in order to evenly distribute the latex compound about the form while the coagulant affects the latex in order to gel the latex film. This rotation equalizes any wet latex runs and assures a more uniform overall gauge in the finished glove. The film is caused to gel more completely by transferring the form through a gelling oven 15 which gels the layer.

After gelling of the latex film layer, the form and layer are immersed in a leaching tank 16 or in a plurality of such tanks. This leaching tank 16 contains hot water which is used to remove any water soluble materials from the deposit.

After removal from the leaching tank, the glove is at what is referred to a green stage. The green glove is dipped into an over-dip tank for flexible top coating. The form is rotated in such a way that the coating is provided uniformly throughout the form. The green glove is passed through curing ovens and the cured glove is ultimately stripped at a stripping booth via manual operation or automatically using a jet process.

It is, therefore, easily seen that the process by which the gloves are made is essentially a series of tanks and associated ovens into which a form, typically made of ceramic or plastic in the shape of a hand, is serially dipped. Each tank contains one of a solution, slurry or latex. The amount of liquid picked up by the forms largely depends on the percent solids, viscosity and times of immersion and withdrawal from each tank.

Referring now to FIGS. 2A, 2B and 2C, it is noted that during the process the form is dipped into the coagulant tank to a level 22. This level is at a point higher on the glove form than level 23 to which the form is dipped into latex (FIG. 2B). Finally, in the lubricous coating over-dip tank, the form is only dipped preferably to a level which covers the fingers and the first portion of the palm at a level 24 (FIG. 2C). By dipping the glove form into the coagulant tank at a level greater than the level intended to dip the form in the latex solution, it is assured that coagulant will be present in order to coagulate the latex onto the form at least to the level selected. The preferred embodiment has an over-dip which only includes the fingers and palm of the glove to create a lubricous surface on the most active portions of the glove while leaving some portions uncoated to permit some degree of frictional control.

Poly(vinyl alcohol) ("PVA") is commercially produced by the hydrolysis of polyvinyl acetate, and is available in a number of grades which vary in the percentage of hydrolyzed acetate groups along the polymer backbone. It is well-known that PVA grades which contain a low amount of residual acetate groups are less soluble in water due to the higher degree of hydrogen bonding which must be disrupted in order for water to solvate the PVA sufficiently. PVA is commercially available in a number of grades in which the degree of hydrolysis varies significantly. These grades are normally referred to as super hydrolyzed (99.3+% hydrolyzed), fully hydrolyzed (98–98.8% hydrolyzed), intermediate hydrolyzed (95.5–97.5% hydrolyzed), and partially hydrolyzed (87–89% hydrolyzed) according to Air Products, a major supplier of PVA products. It is further known that high levels of hydrolysis result in decreased water solubility, increased tensile strength, and increased adhesion to hydrophilic surfaces, whereas lower levels result in increased water solubility, increased flexibility, and increased adhesion to hydrophobic surfaces. It is thus obvious that although high % hydrolysis results in the desired low water solubility required for the casting glove application, it also leads to a coating with higher tensile properties which are undesirable for the reasons discussed above. It is therefore desirable to improve the flexibility of PVA with higher hydrolysis levels while at the same time preserving its water resistance. For these reasons the preferred hydrolysis levels in this invention are those at the high level since they result in a PVA coating with better water resistance and a glove with the desired performance. It has been found that super hydrolyzed and fully hydrolyzed PVA show the preferred water resistance and result in a coating which maintains the desired level of slip during the application of the required number of casting tapes to fully immobilize a fracture.

The amount of rubber used to modify the PVA coating can vary between 5% and 50% based on the weight of PVA and rubber. This is an unexpected result since rubber and PVA are significantly different in chemical nature and would be expected to be incompatible in the dry state when blended, resulting in a material with inhomogeneous properties. Furthermore, the presence of the rubber in the coating serves as an adhesion promoter between the hydrophilic coating and the latex glove onto which it is placed.

Unique to the present invention is a casting glove having lubricity on the surface for easy application of tacky casting tapes, such as polyurethane base synthetic casting tapes. In particular, lubricous surface is a mixture of a hydrophilic material and a rubber based material. The hydrophilic materials may be one of the polymers such as polyvinylalcohols having different levels of hydrolysis (PVA). The preferred polymer is poly(vinyl alcohol) (PVA). The preferred PVA is a poly(vinyl alcohol) with a varying degree of hydrolysis. Examples of such products are D2702 available from H. B. Fuller and Air Products.

The rubber component can be only polymer with a glass transition temperature below room temperature. The natural rubber latex suitable for the present invention may be centrifuged or creamed or the blend of the two latexes. The latex used for the current test was Unitex, centrifuged high ammonia latex marketed by Guthrie Latex, Tucson, Ariz. In certain instances the natural rubber latex can be used without any compounding, it is desirable for the latex to be compounded for proper curing of the natural rubber with vulcanizers, accelerators, antioxidants and other additives. In addition to the natural rubber latex, other lattices of elastomers such as polyurethane, acrylonitrile, copolymers of acrylonitrile-butediene and neoprene can be used for forming the gloves. The preferred material is a natural rubber latex.

To provide a lubricous surface, one method of the present invention is to provide a top coat which is a mixture of the elastic material of the base coat and a hydrophilic coating polymer at a predetermined proportion of the two materials. This top coat is provided by dipping the surface of the base glove into a formulation prepared from the mixture.

One important consideration for the selection of the blending of the two compounds is the compatability of the two compounds so that the blend is stable for sufficient time to permit dipping of the glove. For the blending, the viscosity of the blend should be in a range that permits the top coat to be dipped without back drip. Also, the viscosity should control the thickness of the coating. To control viscosity, thickeners, either water soluble or nonsoluble, can be used. The preferred thickeners, are water dispersable polymers such as polysaccharides, for example, Rhamsan Gum K7C233 or Xantham Gum supplied by Kelco, or fumed silicas such as Cab-O-Sperse A-1695 marketed by Cabot Corp. Depending upon the system it may be desirable to have a surfactant for achieving a homogenous mix of all ingredients. Typically, a nonionic surfactant such as Igepal CO-630 which is an othoxylated nonyl alcohol type, is desirable. The use of a plasticizer is preferable in cases where the hydrophilic coating is rigid. In this case glycerine may be used as a plasticizer without greatly effecting the curing conditions of the glove.

The level of slip of the gloves of the present invention can be easily adjusted. Adjustment is achieved by varying the weight ratio of the rubber and hydrophilic coating materials. A higher level of elastic material, which is hydrophobic, provides a lesser slip. The desirable flexibility of the top coat is to minimize the delamination during the stripping process and donning of the gloves. In addition, the presence of the elastic material in the top coat layer provides a physical bonding between the top coat and the base material.

A test of the slip characteristics was performed as follows:

A cylinder, 24 inches long and 2.75 inches in diameter was wrapped with 4 inch wide fiberglass polyurethane synthetic casting tape. A pair of gloves to be tested was used to apply the casting tape. The preferred casting tape was a Deltalite casting tape marketed by Johnson & Johnson Orthopaedics, Inc. First the tape is dipped into room temperature water and squeezed three times and wrapped around the cylinder. The durability of the gloves is determined as the number of wraps and rolls wrapped with a pair of gloves without exhibiting the tackiness preventing smooth action. In general, when the size of the bare spots in the gloves becomes two by two centimeters, the glove performance becomes unacceptable. The bare spots may be due to erosion of the coating film. In order to help identify the bare spots a color casting tape may be used.

Because of excellent adhesion between the base material and top coating, the level of slip remains unchanged during the normal application of casting tapes. In addition, the glove has longer slip durability then the casting gloves coated with rigid films of polyvinylpyrrolidone. Additionally, the gloves of the invention do not exhibit delamination due to the flexible nature of the slip surfaces.

Since the slippery component of this casting system is contained on the surface of the glove, the current invention does not reduce the cast strength or end laydown. This is a major disadvantage of prior casting tapes incorporating resins with lubricants which diminish the laminating properties of the urethane prepolymer.

EXAMPLES

The following examples illustrate different compositions related to the invention. Example 1 is the control which contains no natural rubber, and shows coating delamination when dry-stripped from the hand forms. Examples 2–4 describe compositions containing various amounts of natural rubber latex in the over-dip solution and all gloves having natural rubber latex in the over-dip display a significant increase in flexibility over the controls and provide gloves which can be stripped without delamination of the applied coating. In addition, the gloves can be donned with considerable stretching without coating delamination. Furthermore, the slip properties of the coatings prepared from Examples 2–4 are sufficient to allow for the application of orthopaedic casting tape without deleterious tackiness.

|  | Coating Composition (wet weight %) | | | |
| --- | --- | --- | --- | --- |
|  | Ex. 1 | Ex. 2 | Ex. 3 | Ex. 4 |
| PVA | 3.5 | 6.7 | 5.8 | 4.7 |
| NR latex | 0 | 2.9 | 3.8 | 4.7 |
| Glycerin | 5.0 | 5.5 | 9.0 | 9.0 |
| Rhamsan gum | 0.4 | 0.2 | 0.3 | 0.4 |
| Glutaraldehyde | 0.08 | 0.08 | 0.8 | 0.08 |
| Water | 90.8 | 84.6 | 81.1 | 81.0 |
| Igepal | 0.04 | 0 | 0 | 0 |
| Cab-O-Sperse | 0.2 | 0 | 0 | 0 |

The PVA normally used in these examples is designated by the trade designation D2702, available from H. B. Fuller Co. This product code identifies a fully hydrolyzed grade of PVA and may be represented by Air Products, Airvol 325–350 series. The PVA may contain a small percentage of bacteriostat (i.e., glutaraldehyde for example) and a defoamer in the proprietary mixtures. "Cab-O-Sperse A-1695" refers to a colloidal dispersion of fumed silica in water. This dispersion is pH adjusted with ammonium hydroxide. The material is available from Cabot Corp., Cab-O-Sil Division. Igepal CO-630 is a surfactant of the othoxylated nonyl alcohol type.

A similar example, using a synthetic rubber latex base is shown as Example 5.

EXAMPLE 5

A nitrile rubber casting glove was prepared by using a nitrile rubber modified top coating consisting of the following components:

|  | Coating composition wet weight % |
| --- | --- |
| PVA | 3.2 |
| Nitrile rubber latex | 1.3 |
| Glycerin | 3.2 |
| Rhansam gum | 0.4 |
| Glutaraldehyde | 0.1 |
| Water | 91.6 |
| Igepal | 0.02 |
| Cab-O-Sperse | 0.2 |

The above coating was used to coat nitrile rubber gloves and cured to give finished gloves. The gloves showed excellent stretch properties and no delamination of the PVA coating when they were removed from the glove forms. The durability of the gloves was sufficient to apply numerous casting tapes and did not result in adhesion between the gloves and the tape.

As can be seen from the above, a glove having a lubricous surface may be provide for applying an orthopaedic bandage. The glove has a base material of flexible elastic material which defines a hand-receiving portion and has a coating of lubricant material in mixture with a major constituent of the base material coated thereover. The base material may be, for example, natural rubber latex, synthetic rubber or nitrile rubber. The glove lubricant is preferably a hydrophilic lubricant and is preferred to be polyvinyl alcohol. In such a situation a preferred coating is a mixture of uncured natural rubber latex and polyvinyl alcohol. However, a mixture of uncured synthetic rubber and polyvinyl alcohol or a mixture of uncured nitrile rubber and polyvinyl alcohol may be used in appropriate situations.

Alternatively, the hydrophilic lubricant may be polyvinylpyrrolidone or polyethylene oxide. Thus a resulting glove could have a substantially dry mixture of cured natural rubber latex and polyvinylpyrrolidone coated thereon, or may have a substantially dry mixture of cured natural rubber latex and polyethylene oxide.

The coating may comprise a mixture of natural rubber latex and polyvinyl alcohol having from approximately 5% to 50% by weight natural rubber latex and from 95% to 50% by weight polyvinyl alcohol of the natural rubber latex and polyvinyl alcohol total weight. This mixture may also include glycerin or Rhamsan gum or both as a thickener.

In an alternative embodiment, the glove itself is made from a base material which is itself a mixture of a flexible elastic material and a hydrophilic lubricant material. The glove may, for example, be made of natural rubber latex and the hydrophilic lubricant material may be polyvinyl alcohol. Alternatively, the hydrophilic lubricant material may be polyvinylpyrrolidone or polyethylene oxide.

We claim:

1. A glove having a lubricous surface for use in applying an orthopaedic casting bandage comprising:
   a) a base material of flexible elastic material defining a hand receiving portion; and,
   b) a coating of lubricant material in mixture with a major constituent of said base material.

2. The glove according to claim 1 wherein said base material comprises natural rubber latex.

3. The glove according to claim 1 wherein said base material comprises synthetic rubber.

4. The glove according to claim 1 wherein said base material comprises nitrile rubber.

5. The glove according to claim 1 wherein said lubricant is a hydrophilic lubricant.

6. The glove according to claim 5 wherein said hydrophilic lubricant is poly(vinyl alcohol).

7. The glove according to claim 6 wherein said coating is a mixture of uncured natural rubber latex and said poly(vinyl alcohol).

8. The glove according to claim 6 wherein said coating is a mixture of uncured synthetic rubber and said poly(vinyl alcohol).

9. The glove according to claim 6 wherein said coating is a mixture of uncured nitrile and said poly(vinyl alcohol).

10. The glove according to claim 1 wherein said coating is a substantially dry mixture of cured natural rubber latex and poly(vinyl alcohol).

11. The glove according to claim 5 wherein said hydrophilic lubricant is polyvinylpyrrolidone.

12. The glove according to claim 5 wherein said hydrophilic lubricant is polyethylene oxide.

13. The glove according to claim 11 wherein said coating is a substantially dry mixture of cured natural rubber latex and polyvinylpyrrolidone.

14. The glove according to claim 11 wherein said coating is a substantially dry mixture of cured natural rubber latex and polyethylene oxide.

15. The glove according to claim 2 wherein said coating comprises a mixture of natural rubber latex and poly(vinyl alcohol) having from 5% to 50% by weight of natural rubber latex and from 95% to 50% by weight poly(vinyl alcohol) of natural rubber latex and poly(vinyl alcohol) total weight.

16. The glove according to claim 15 wherein said coating includes glycerin and a thickener.

17. The glove according to claim 16 wherein said thickener is Rhamsan gum.

18. A glove having a lubricous outer surface for use in applying orthopaedic casting tapes comprising a base material mixture including flexible elastic material and a hydrophilic lubricant material forming a hand receiving portion.

19. The glove according to claim 18 wherein said flexible elastic material is natural rubber latex.

20. The glove according to claim 19 wherein said hydrophilic lubricant material is poly(vinyl alcohol).

21. The glove according to claim 19 wherein said hydrophilic lubricant material is polyvinylpyrrolidone.

22. The glove according to claim 19 wherein said hydrophilic lubricant material is polyethylene oxide.

* * * * *